US005666404A

United States Patent [19]
Ciccotelli et al.

[11] Patent Number: 5,666,404
[45] Date of Patent: Sep. 9, 1997

[54] DEVICE FOR TELEPHONE MONITORING OF PATIENTS HAVING PERIPHERAL ARTERIAL OCCLUSIVE DISEASE

[75] Inventors: Ernest J. Ciccotelli, Norwich, Vt.; Edward A. Gilchrest, Jr., Southbury, Conn.

[73] Assignee: Manfred Asrican, Greenwich, Conn.

[21] Appl. No.: 660,929

[22] Filed: Jun. 10, 1996

Related U.S. Application Data

[63] Continuation of Ser. No. 925,744, Aug. 7, 1992, abandoned, which is a continuation-in-part of Ser. No. 738,263, Jul. 31, 1991, abandoned.

[51] Int. Cl.⁶ ................................. H04M 11/00
[52] U.S. Cl. ................ 379/106.02; 379/93.37; 128/681; 128/904
[58] Field of Search .............. 379/38, 102, 106, 379/107, 93, 99; 128/904, 680–683, 715

[56] References Cited

U.S. PATENT DOCUMENTS

| | | | |
|---|---|---|---|
| 3,552,381 | 1/1971 | Burns et al. | 128/715 |
| 3,552,385 | 1/1971 | Jansen | 128/680 |
| 3,872,252 | 3/1975 | Malchman et al. | 379/38 |
| 4,078,551 | 3/1978 | Wohltjen et al. | 128/681 |
| 4,170,226 | 10/1979 | Albainy et al. | 128/681 |
| 4,830,018 | 5/1989 | Treatch | 128/904 |
| 4,953,557 | 9/1990 | Frankenreiter et al. | 128/680 |
| 4,974,607 | 12/1990 | Miwa | 128/904 |
| 5,031,630 | 7/1991 | Hirano et al. | 128/680 |

OTHER PUBLICATIONS

J. L. Crouch et al, "Electrocardiograms By Telephone", Bell Laboratories Record, Feb. 1966, pp. 32–47.

*Primary Examiner*—Wing F. Chan
*Attorney, Agent, or Firm*—Charles E. Temko

[57] ABSTRACT

A device for post-operative monitoring by telephone the condition of patients having peripheral arterial occlusive disease. A first embodiment of the device includes an inflatable cuff incorporating a piezo electric film element which generates a signal of varying amplitude. A pressure sensor communicating with the cuff allows transmission of the signal only at a pre-determined cuff pressure. The signal is frequency modulated and transmitted through a modem over the telephone line of the patient to the office of the physician, where it is demodulated to provide a varying direct current for operating a chart recorder. Usage of the device need require only five to ten minutes a day, and the patient can telephone the office of the physician prior to transmission of the signal to identify the patient. In a second embodiment, the piezo electric signal is substituted by a pneumatically generated signal.

2 Claims, 11 Drawing Sheets

DEVICE FOR TELEPHONE MONITORING OF PATIENTS HAVING PERIPHERAL ARTERIAL OCCLUSIVE DISEASE

RELATED APPLICATION

This application is a continuation of Ser. No. 07/925,744, filed Aug. 7, 1992 abandoned which is a continuation in part of our application Ser. No. 07/738,263, filed Jul. 31, 1991, abandoned.

BACKGROUND OF THE INVENTION

This invention relates generally to the field of medical data gathering devices which permit telephone transmission of clinical data or parameters from the patient's location to a hospital or physicians office. Information so transmitted is not necessarily definitively diagnostic, but is intended to provide remote patient observation to indicate if and when a patient should be recalled for further examination.

More particularly, the invention relates to the management and post operative monitoring of patients who have undergone a corrective surgical procedure for peripheral arterial occlusive disease. A commonly employed surgical procedure is the insertion of an arterial graft or by-pass or, where appropriate, a balloon catheter may be employed to expand a stenotic i.e. narrowed region in an arterial wall. While initially effective in a great majority of patients, such interventional procedures do carry with them a definite failure rate. Arterial grafts can and do fail, and re-stenosis or occlusion occurs in a percentage of patients, with potentially grave consequences. As is often the case, patient safety and surgical long term outcome are greatly enhanced by early detection of the tendency of the graft or by-pass to fail. Patients are routinely re-evaluated shortly after the completion of the procedure. However, it is quite impractical, and far too expensive to provide a high frequency of patient supervision by office or hospital visits subsequent thereto. There thus arises a need for monitoring of the condition of the patient at frequent e.g. daily intervals without the necessity of the patient leaving his home.

SUMMARY OF THE INVENTION

Briefly stated, the invention contemplates the provision of an improved device and method of use by the patient, who is typically an elderly and frail individual wherein the transmitting part of the device is applied by the patient to the body whereby the desired information is transmitted over a subscriber telephone line for review by the physician in his own office after the information has been graphed.

To this end, the device includes a pressure cuff such as commonly employed in the measurement of blood pressure on the arm which contains a distensible bladder of neoprene or other elastic material which forms a principal part of the patient unit. A piezo-electric flexible strip is affixed to the inner surface of the cuff in such manner that a pressure change against the inner surface of the cuff generates a voltage proportional to the pressure change.

In order to achieve reproducible electric output signals from the piezo-electric strips, or transducer, the cuff bladder is inflated to a standardized pressure, i.e. 60 mm Hg. In the preferred embodiment this is accomplished by the combination of a hand inflation bulb as commonly used on blood pressure cuffs, together with an excess pressure relief valve set for the pre-determined value. A small electric bulb or light emitting diode powered by a dry cell illuminates when the predetermined pressure has been attained. This arrangement assures that the contact pressure of the bladder of the pressure cuff against the skin will remain constant from one data transmission to the next, wherein trends or relative changes in the generated voltage, and therefore the related pulse amplitude, can be observed consistently. During a cardiac cycle, as the regional hemodynamic perfusion in an anatomic segment such as the ankle region varies, the pulsatile changes transmitted through the skin of the patient to the piezo-electric strip affixed to the cuff, and the resulting varying voltage, is fed to signal leads communicating with a modem. Most conveniently, the modem device provides a base or cradle for the telephone hand set. Prior to transmission, the analog voltage is converted to a frequency modulated signal. The frequency modulated signal is transmitted over the telephone system to a corresponding device in the office of the physician which also includes a telephone modem, a demodulation circuit, and a medical type chart recorder.

In a second embodiment by monitoring the changes in the air pressure inside the bladder contained in the cuff assembly using an air pressure transducer in the pneumatic system of the device, a similar result is obtained.

BRIEF DESCRIPTION OF THE DRAWINGS

In the drawings, to which reference will be made in the specification, similar reference characters have been employed to designate corresponding parts throughout the several views.

DETAILED DESCRIPTION OF THE DISCLOSED EMBODIMENT

Figure 1:
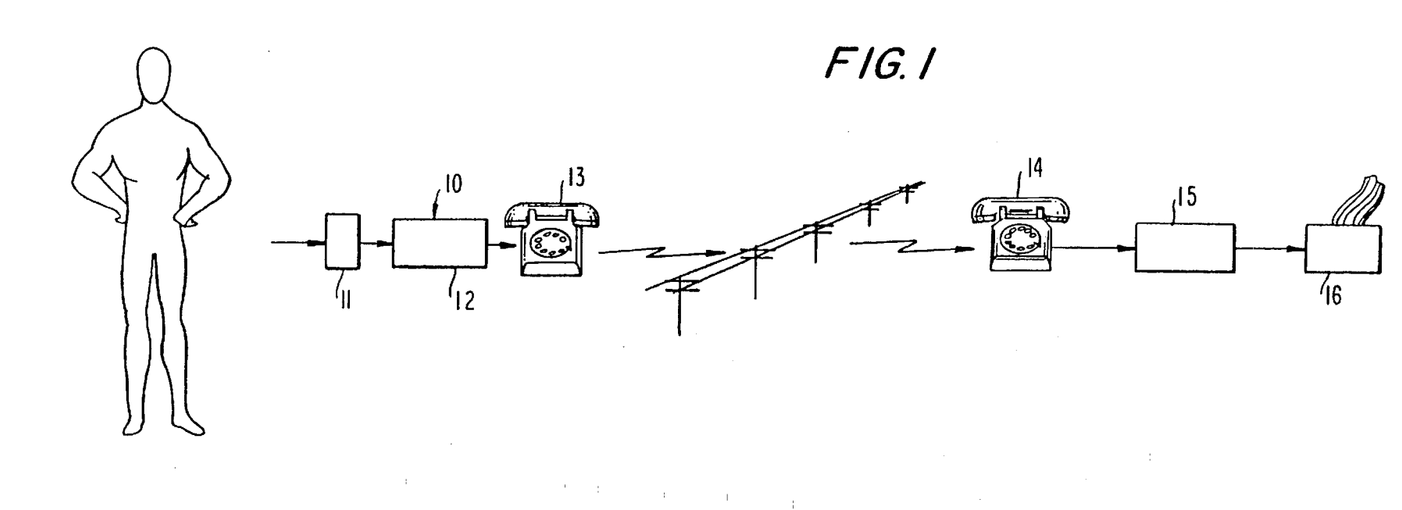
FIG. 1 is a schematic block diagram of an embodiment of the invention.

Referring to FIG. 1, device, generally indicated by reference character 10 comprises a cuff element 11 including a modem 12 with accompanying circuitry, a transmitting telephone 13, a receiving telephone 14 and corresponding modem 15 as well as chart recorder 16.

Figure 2:
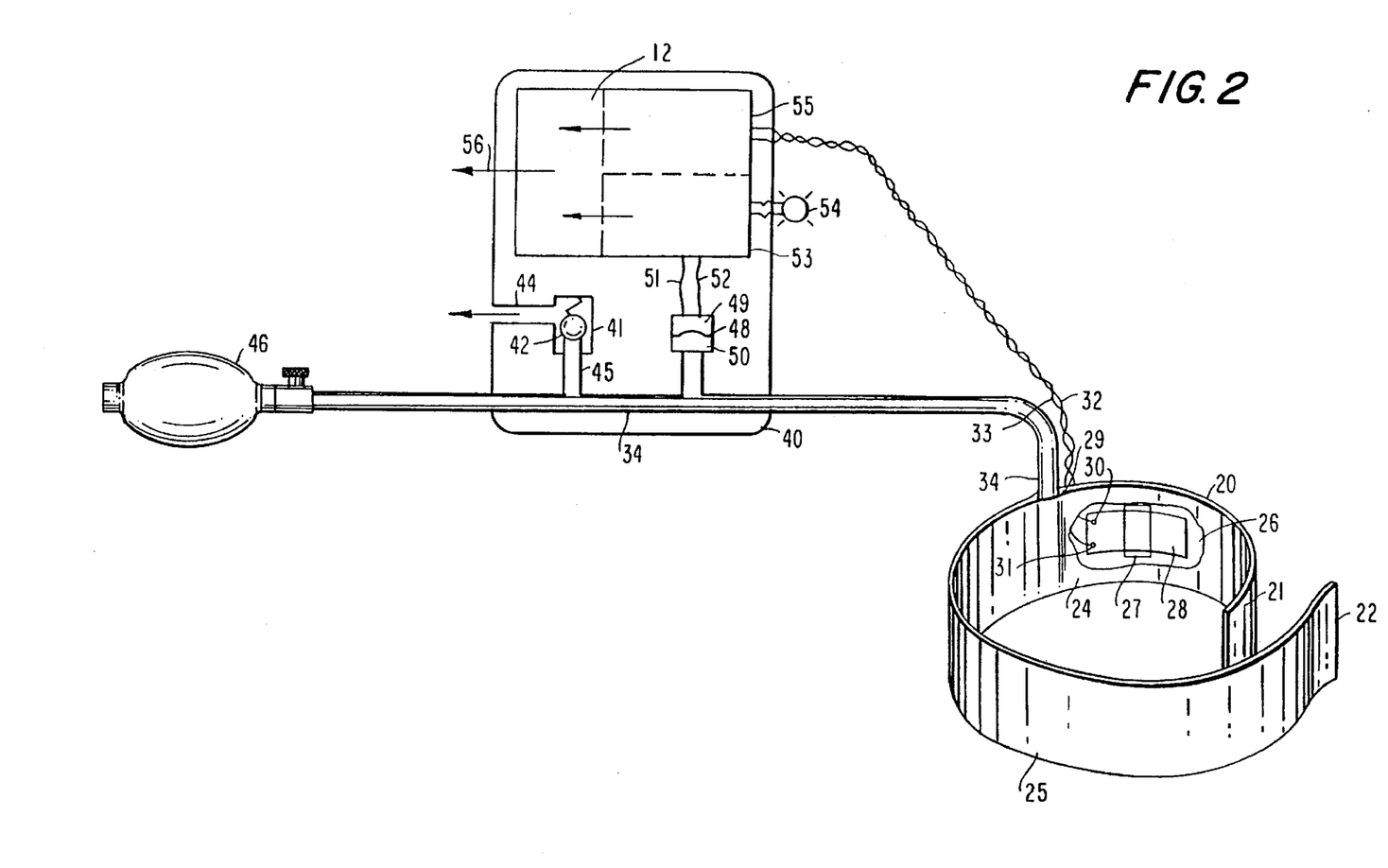
FIG. 2 is a schematic block diagram showing the details of the transmitting portion of the device.
Figure 3:
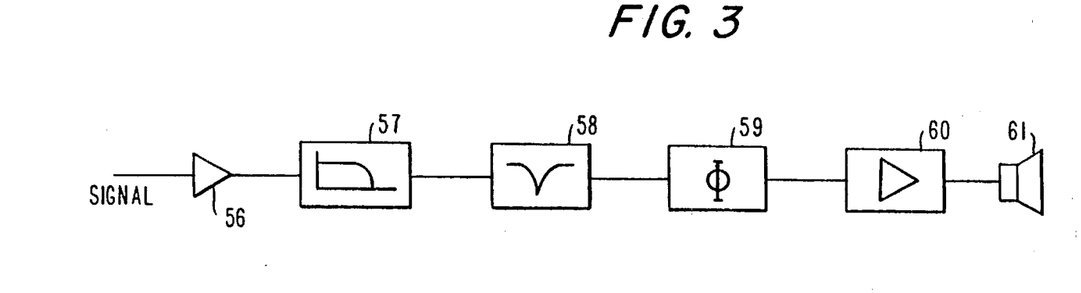
FIG. 3 is a block diagram showing the electronic components of the transmitting part of the device.

The cuff element 11 is generally conventional, including an elongated body 20 terminating in overlapping end portions 21 and 22 which are commonly provided with hook and pile adjustable fastening means (not shown). Inner and outer surface members 24 and 25 enclose an inflatable member 6 having an inner surface 27 which mounts one or more small piezo-electric planar films 28 using a flexible adhesive (not shown). An edge opening 29 provides egress from a pair of output terminals 30 and 31 through conductors 32 and 33. It provides a like function for an inflating tube 34 which extends through a rectangular housing 40 which provides a base for a conventional telephone. The housing 40 includes a cavity 41 forming part of a pressure relief valve 42 of known type including an exhaust vent 44 and a passage 45 extending to communicate with the tube 34. Also disposed within the housing 40 is a pressure sensor 48 including a chamber 49 enclosing a floating piston 50 which when activated serves to interconnect first and second conductors 51 and 52 to a circuit schematically indicated by reference character 53. This circuit includes a three color indicator light 54 in the form of an incandescent bulb or a light emitting diode, and other switches which control the operation of the plethysmographic circuits generally indicated by reference character 55. The output of the circuits 55 is to a conventional telephone modem 12 connected to the patient's telephone subscriber circuit. The circuits 55 are of known type and are schematically illustrated in FIG. 3. The piezo-electrically generated signal is first fed to an input amplifier 56, and serially to a low pass filter 57, a 60 Hz notch filter 58, a voltage-controlled oscillator 59, and a power amplifier 60 which inputs to an acoustic coupling 61. The output of the circuits 55, generally indicated by reference character 56 can either digitize the analog signal received from the piezo-electric element 28, or may receive the signal in frequency modulated form.

At a remote location, i.e. the office of the attending physician, a separate subscriber circuit is provided with the modem 15, the output of which is an analog voltage which controls the stylus (not shown) on the chart recorder 16.

Figure 5:
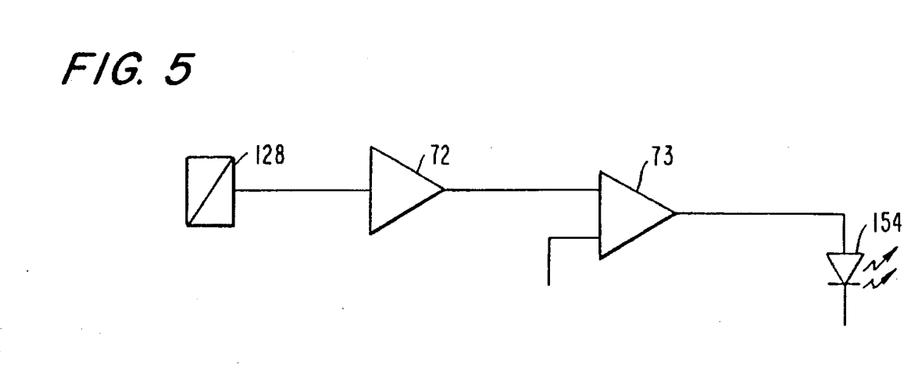
FIG. 5 is a schematic block diagram showing the electronic components of the second embodiment.
Figure 6:
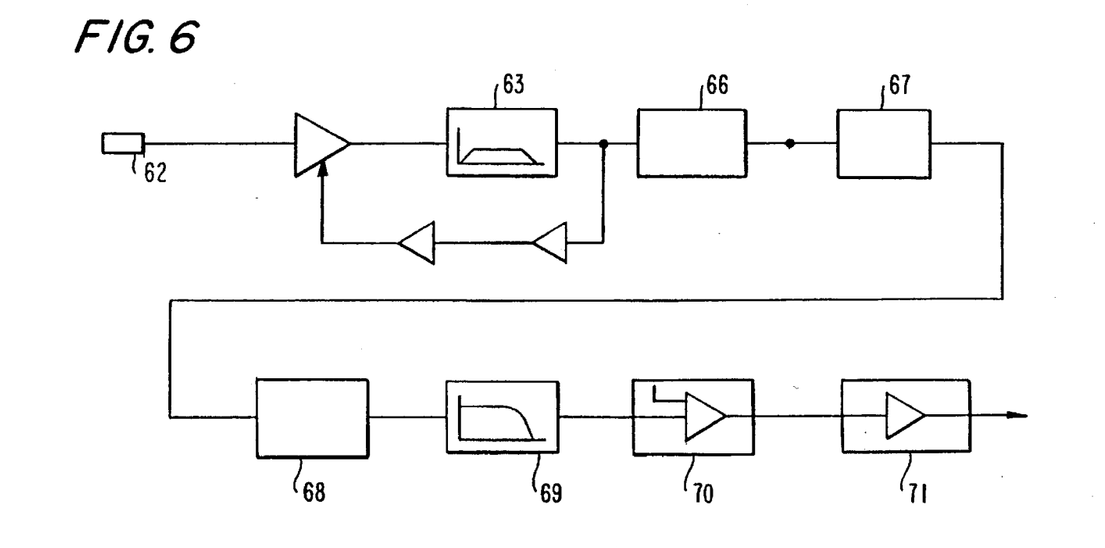
FIG. 6 is a schematic block diagram showing the electronic components of the receiver portion common to both the first and second embodiments.
Figure 7A:
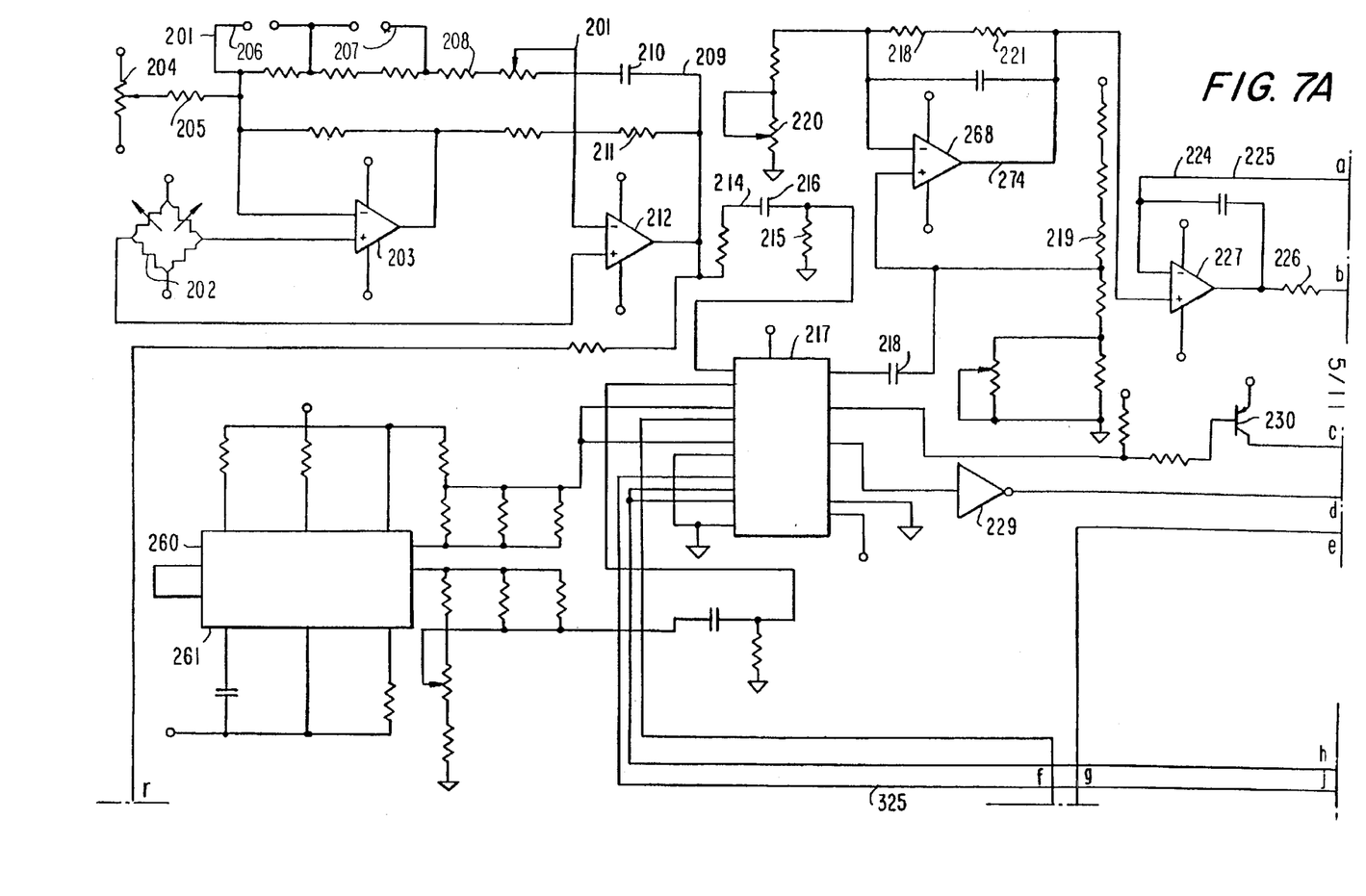
FIGS. 7a, 7b, 7c and 7d constitute a detailed schematic diagram of the electronic components of the transmitting part of the device in accordance with the second embodiment.
Figure 7B:
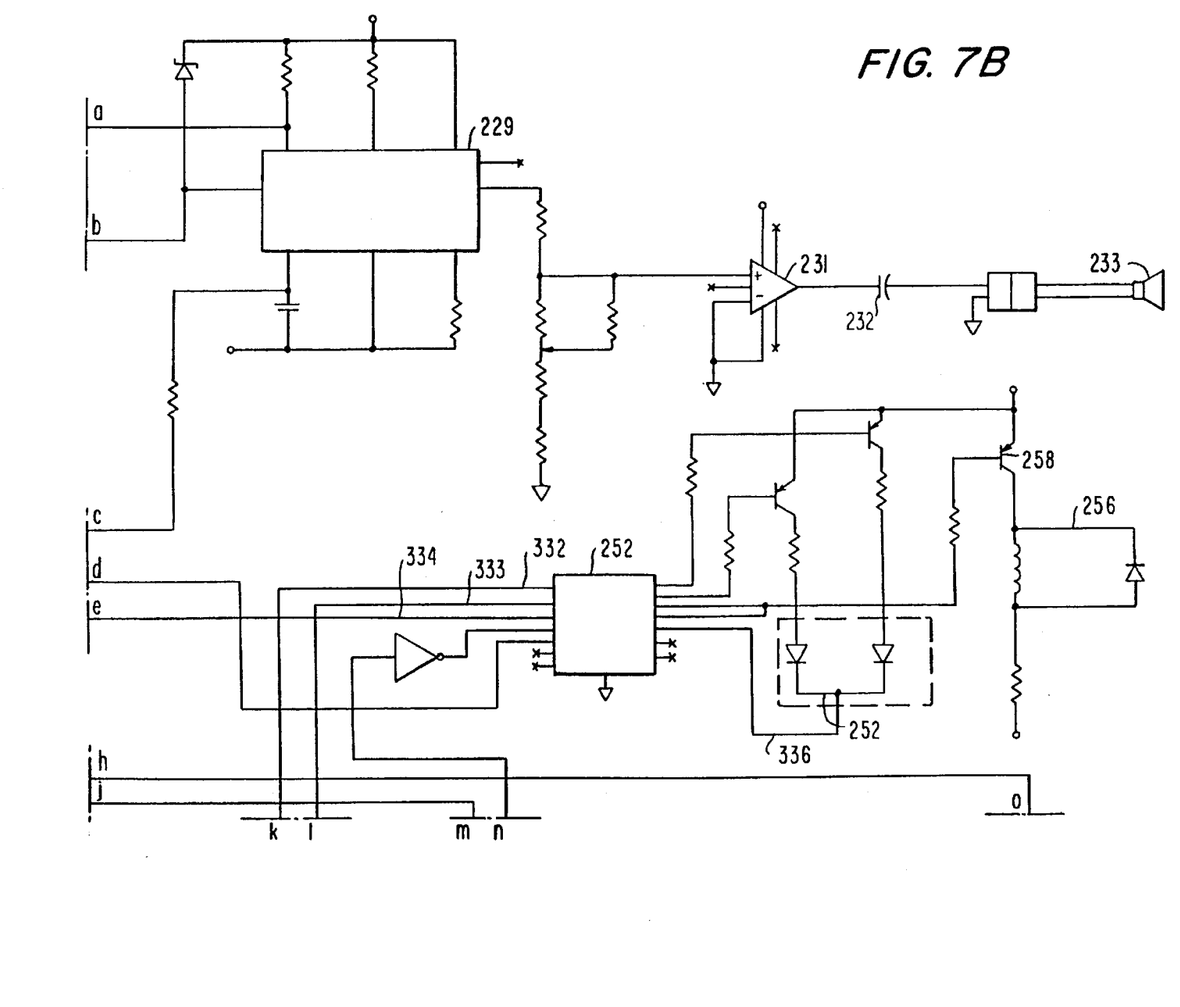
Figure 7C:
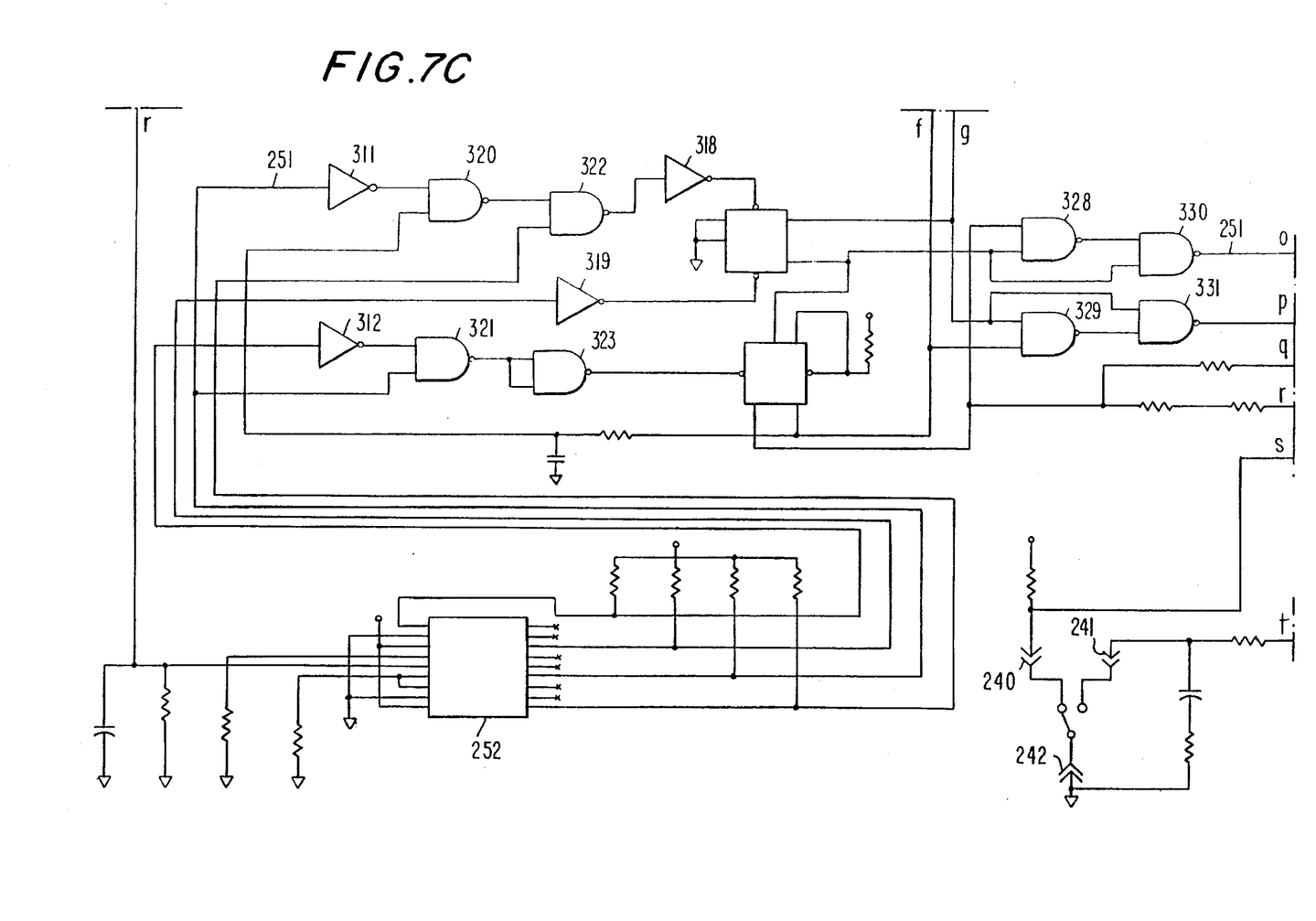
Figure 7D:
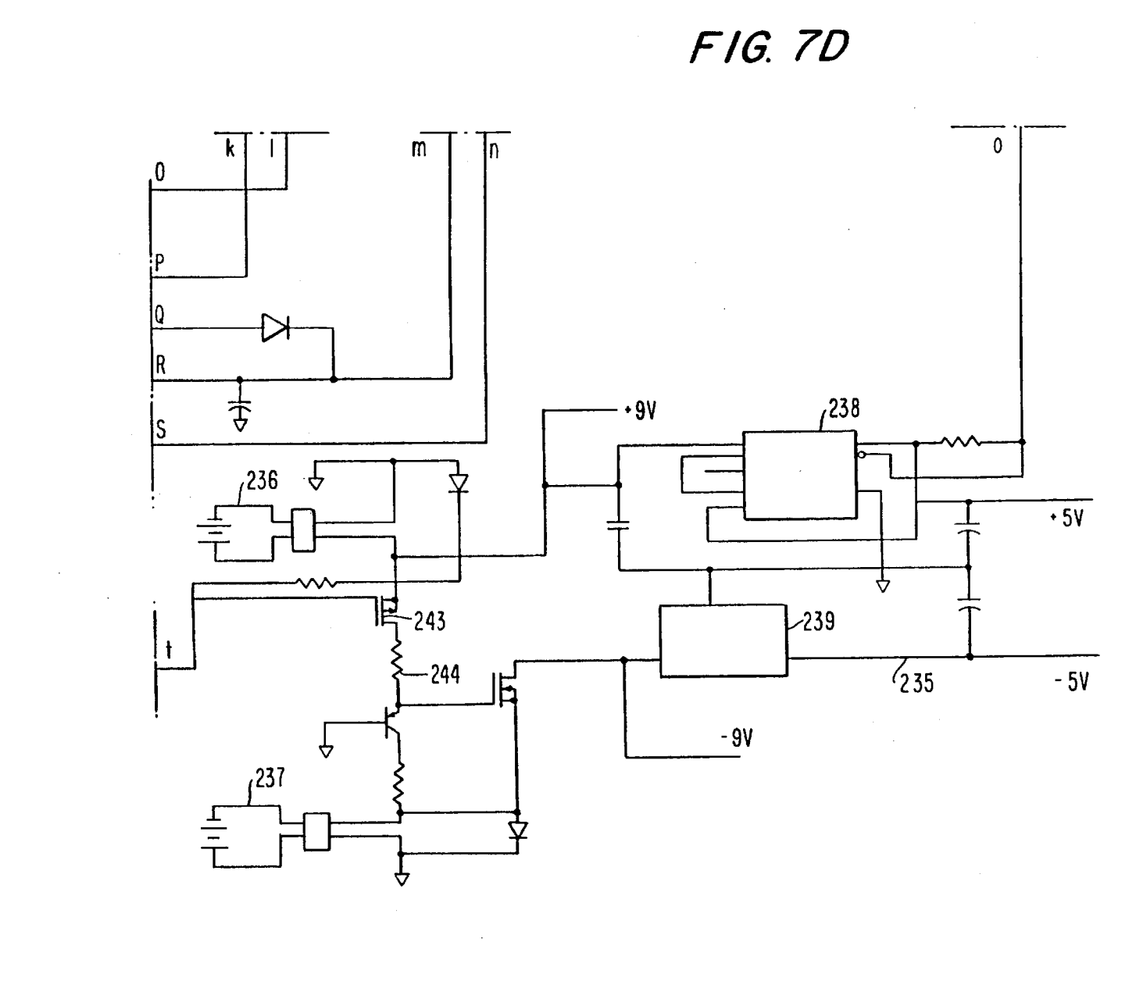

FIG. 5 schematically illustrates the electronic components of the receiver portion of the device which includes a microphone 62, serially feeding a low pass filter 63, the output of which is partially fed to a feed back loop including an amplifier 64 and a detector 65, which loop serves as an automatic gain control. The output also serially feeds a 60 Hz notch filter 66 which eliminates AC hum, and a limiter amplifier 67 which removes any amplitude variation from frequency modulated signals. The signal is then fed to a phase lock loop demodulator 68, a further filter 69 to remove any PPL artifacts, a DC restoration element 70 and an output amplifier 71 which provides sufficient current to power the chart recorder.

Operation is commenced by the patient engaging the cuff element 11 with a limb, typically at an ankle, following which he inflates the cuff element using a bulb type pump 46 continuing operation until the pressure sensor indicates by illuminating the indicator light 54 that proper operating pressure has been reached. At this point, he dials the telephone at the remote location, and identifies himself, thereafter receiving instructions to dial a separate line which includes the modem 15. Since the cuff element and accommodating circuitry is in operation, the recorder 15 may commence operation as soon as the modem line goes "off hook". This operation is continued for a sufficient period of time to get a representative sample for subsequent study, normally a minute or two, following which the patient hangs up his telephone, bleeds the cuff element and removes the cuff.

If during transmission the system loses pressure, the indicator light 54 will extinguish, advising the patient to check the system before resuming transmission.

Turning now to the second embodiment of the invention (FIG. 4), parts corresponding to those of the first embodiment have been designated by similar reference characters with the additional prefix "1".

Figure 4:
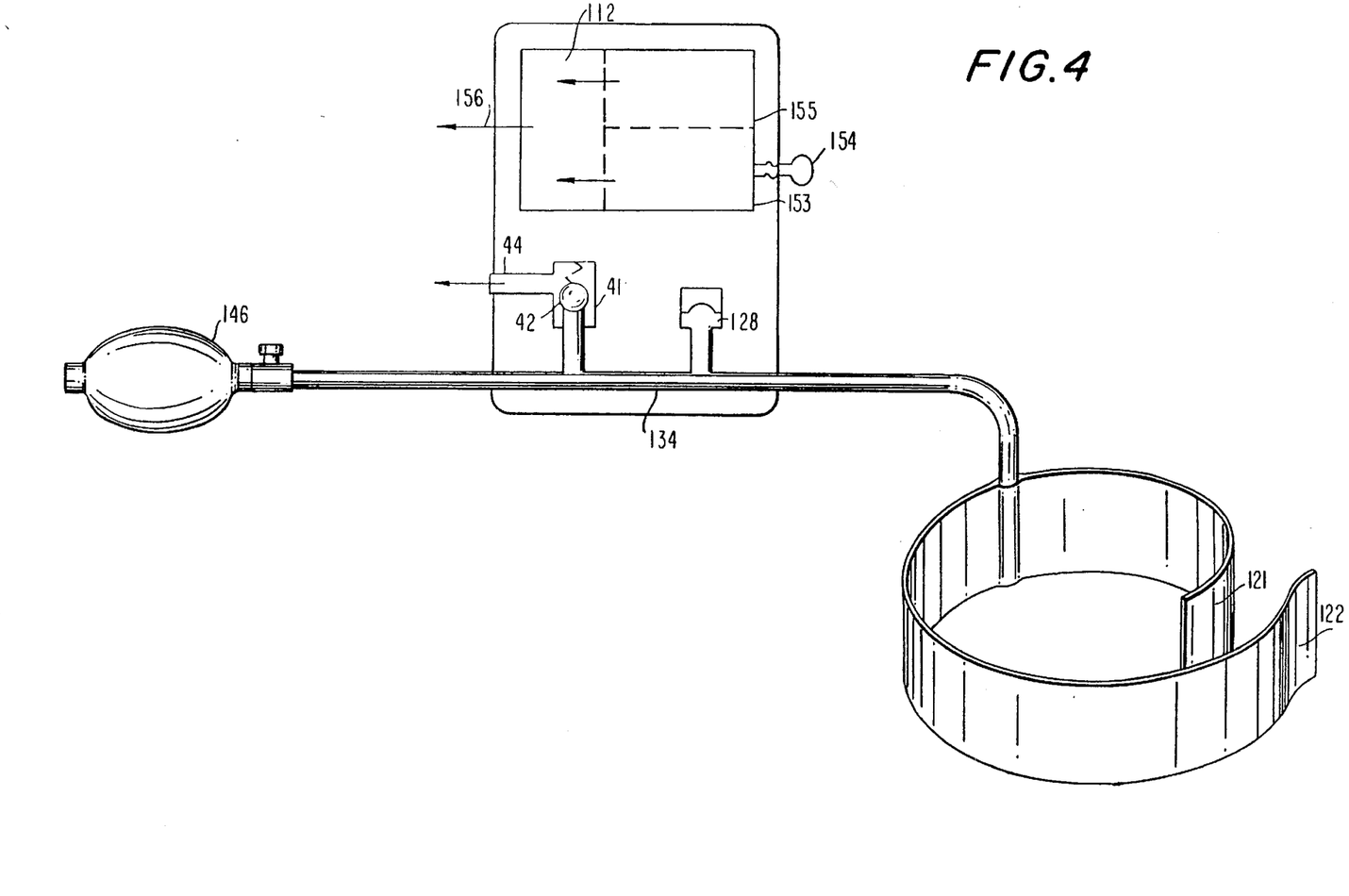
FIG. 4 is a schematic block diagram of a second embodiment of the invention.

In the second embodiment, the use of the piezo-electric signal generation is substituted by a pneumatically generated signal. This is provided by a pressure transducer 128 which feeds an amplifier 72, the output of which is fed to a reference comparator 73, thence to the light emitting diode 154 and thence to the components shown in FIG. 3.

FIG. 7 illustrates in greater detail the electronic components of the patient unit in accordance with the second embodiment. It will be understood that the disclosure is also applicable to the first embodiment by substituting for the pressure sensor 202, a simple terminal (not shown) for directly receiving an electrical signal from the cuff element.

As illustrated in FIG. 7, pulsatile pressure is initially received by a pressure sensor 202 forming part of a front end 201. This is typically a SENSYM SCX05DNC, or a Honeywell microswitch 24PCBBB2G having an operational range between 0–5 pounds per square inch. The Sensyn has a nominal gain of 12 microvolts per square inch with a 12 volt supply. In the present application, the supply voltage will be ±5 or 10 volts giving a sensitivity of 10 mV/psi. For an output of 2.5 volts with a pressure input of 65 mmHg or 1.25 psi the gain of the differential front end needs to be:

$$\text{Gain} = 2.5 \text{ volts} \times 1000 \text{ mv/volt}/(1.25 \text{ psi} \times 10 \text{ mV/psi}) = 200$$

The Honeywell sensor has a nominal gain of 23 mV/psi with a 10 volt supply. For an out of 5 volts with a pressure input of 65 mm Hg or 1.25 PSI the gain of the differential front end need to be:

$$\begin{aligned}\text{Gain} &= (2.5 \text{ volts} \times 1000 \text{ mv/volt})/(1.25 \text{ psi} \times 23 \text{ mV/psi}) \\ &= 173.9\end{aligned}$$

The sensor 203 feeds a first comparator amplifier 203 which receives its input from an offset adjustment 204 through a fixed resistor 205. A pair of gain select jumpers 206 and 207 provide gain adjustment. A trimming potentiometer 208 is connected to a 50 Hz low pass filter 209 including capacitor 210 and resistor 211 the output of which is fed to a second comparator 212.

Communicating with the front end is a low pass filter 214, including a resistor 215 and capacitor 216 connected to an integrated circuit 217 forming part of a multiplex stage which determines in which mode the device is operating. It will direct either the patient pressure wave form, a 2 Hz calibration signal, or it will send a signal identifying a low battery condition.

The output of the multiplex feeds another high pass filter consisting of a 2.2 uf capacitor 218 and an equivalent resistance 219. This gives a −3db point of:

$$\begin{aligned}F_{-3db} &= 1/(2 \times Pi \times 2.2 \times 10^{-6} \times 5 \times 10^{5}) \\ &= 0.144 \text{ Hz}\end{aligned}$$

This gives less than 2% gain error at the frequency band of the signals 1 Hz to 10 Hz. The high pass filter contains a potentiometer 220 to adjust the center frequency of the system to 1 kHz.

A second gain stage 224 includes an low pass filter including capacitor 225 and resistor 226. The low pass filter is set for 212 Hz.

Frequency generation is provided by an ICL8038 function generator 228 and an operational amplifier 229. The function generator and operational amplifier are configured to give good linearity of the operating frequency range of 900 Hz to 1100 Hz. A transistor 230 is used to shut down the generator when the cuff pressure is not correct.

A power amplifier 231 consists of an LM386 low voltage audio power amplifier which drives through a capacitor 232 to a speaker 233.

The power supply 235 on the patient unit is preferably battery powered for simplicity by means of first and second 9 volt batteries 236 and 237, and includes first and second regulators 238 and 239. Telephone switches, 240, 241 and 242 are part of the telephone receiver hand set, and are closed when the telephone goes "off hook" thereby activating field effect transistors 243 and 244. In the patient unit, only 5 volt power is required.

The control of the solenoid output and display is accomplished using the output from the front end compared to references using an LM3914 bar graph display driver 250 as level comparators. The thresholds are set as follows:

| | |
|---|---|
| Yellow | From turn on to 1.44 psi (75 mmHg) |
| Red | Over 1.44 psi |
| Green | Operational range (60 mmHg to 70 mmHg) and Solenoid off |
| Solenoid | Off from turn on to 1.44 psi, goes on over 1.44 psi, turns off at 65 mmHg, turns back on at 70 mmHg. Turns on for 2 seconds when phone is removed from unit |
| Output | On when green LED is on |

The Solenoid 256 is activated using an integrated circuit 252 (ULN2003) which drives a transistor 258.

The LM3914 is an LED display driver which in the the present embodiment is used in a very novel manner. The LM3914 is normally used to drive a 10 element LED bar graph display.

In a standard configuration the first LED would turn on at an input to the LM3914 of 0.25 volts, with each consecutive LED turning on in 0.125 volt increments with the last LED turning on at 1.25 volts.

The desired cuff pressure is 65 ±mmHg. When inflating the cuff, it is necessary to make sure the pressure exceeds this level before activating the solenoid relief valve to prevent any pressure fluctuations from causing erratic performance. Therefore, that activation point is set at 75 mmHg. But once the solenoid is disabled at 65 mmHG and the device starts transmitting data, it is necessary to make sure that the pressure does not drift above 70 mmHG, thus requiring a secondary solenoid activation at that point. It is also necessary that the data transmission be interrupted if the pressure falls below 60 mmHg with an indication to the patient to reinflate the cuff.

This control needs to be done in a relatively simple and inexpensive way in the present device. To accomplish this, the standard LM3914 circuit is modified to give trip points at 60, 65, 70 and 75 mmHg. This is combined with logic circuitry and a multiplex to provide a circuit which performs the above parameters.

The pressure transducer output is amplified by amplifier 212 to give an output at pin 7 of 2.5 volts for a 65 mmHg input (0.0384 volts/mmgH). The output is divided down through resistor 305 and resistor 306 for a multiplier of 0.434. This provides a 0.0167 volts/mmHg scale at the LM3914 input. The addition of capacitor 307 adds a low pass function set at 0.34 Hz to prevent any pressure fluctations from causing erratic performance.

The highest trip point is:
1.25 volts/0.0167 = 74.9 mmHg
with a range of
(1.25 volts × 34.8 k)/44.8 k = 0.971 (new "zero" point)
1.25 volts − 0.91 volts = 0.279 volts
and a scale of
0.279 volts/10 = 0.279 volts per step
or 0.0279 volts/0.0167 volts/mmHg = 1.67 mmHg per step
resistor 259 sets the first trip point at
(1.25 volts × 34.8 k)/44.8 k + 0.0279 volts = 1.00 volts
1.00 volts/(0.0167 volts/mmHg) = 59.9 mmHg (the lowest trip point)
giving the steps as:
59.9 mmHg
61.6
63.2
64.9
66.6
68.3
69.9
71.6
73.3
75.00

The outputs of the LM3914 are pulled up with resistors 305, 306, 307, and capacitor 308 and fed to the logic circuitry 251, consisting of amplifiers 311 and 312, resistors 313, 314, 315, 316 and 317, amplifiers 318 and 319, and gates 320, 321, 322, 323; and gates 328, 329, 330 and 331. The logic circuitry is configured to have five ouputs; green LED 332, Red LED 333, Control Red 334, Green LED delayed 335, and an Output Enable Line 336. The ouputs control the multiplex and the driver 252. The individual outputs have the following characteristics:

| Condition 1 Inflation to 75 mmHg | |
|---|---|
| Green LED: | High |
| Red LED: | High |
| Control Red: | Low |
| Green LED Delayed: | Low |
| Output Enable: | Low |
| Condition 2 Above 75 mmHG to 65 mmHg | |
| Green LED: | Low |
| Red LED: | High |
| Control Red: | High |
| Green LED Delayed: | Low |
| Ouput Enable: | Low |
| Condition 3 65 mmHg | |
| Green LED: | High |
| Red LED: | Low |
| Control Red: | Low |
| Green LED Delayed: | Low then High after 5 seconds |
| output Enable: | High |
| Condition 4 60 mmHg to 70 mmHg | |
| Green LED: | High |
| Red LED: | Low |
| Control Red: | Low |
| Green LED Delayed: | High |
| Output Enable: | High |
| Condition 5 Below 60 mmHG | |
| Green LED: | High |
| Red LED: | High |
| Control Red: | Low |
| Green LED Delayed: | Low |
| Output Enable | Low |
| Condition 6 Above 70 mmHg (from condition 4) | |
| Green LED: | Low |
| Red LED: | High |
| Control Red: | High |
| Green LED Delayed: | Low |
| Output Enable | Low |

Logic circuitry 251 of known type controls the light emitting display 254 and the status of the solenoid 256. This circuitry is governed by signals from the front end indicating the cuff pressure, so that transmission will be interrupted when this pressure falls below the standard transmitting pressure, and pressure is bled from an excess value down to the standard value.

A calibration circuit 260 includes a sine wave generator 261. This circuit modulates the carrier using a 2Hz sine wave. This is displayed on the receiving unit and indicates if any transmission problems exist. The signal is activated once the green light is on and persists for approximately 2 to 3 seconds.

Figure 8A:
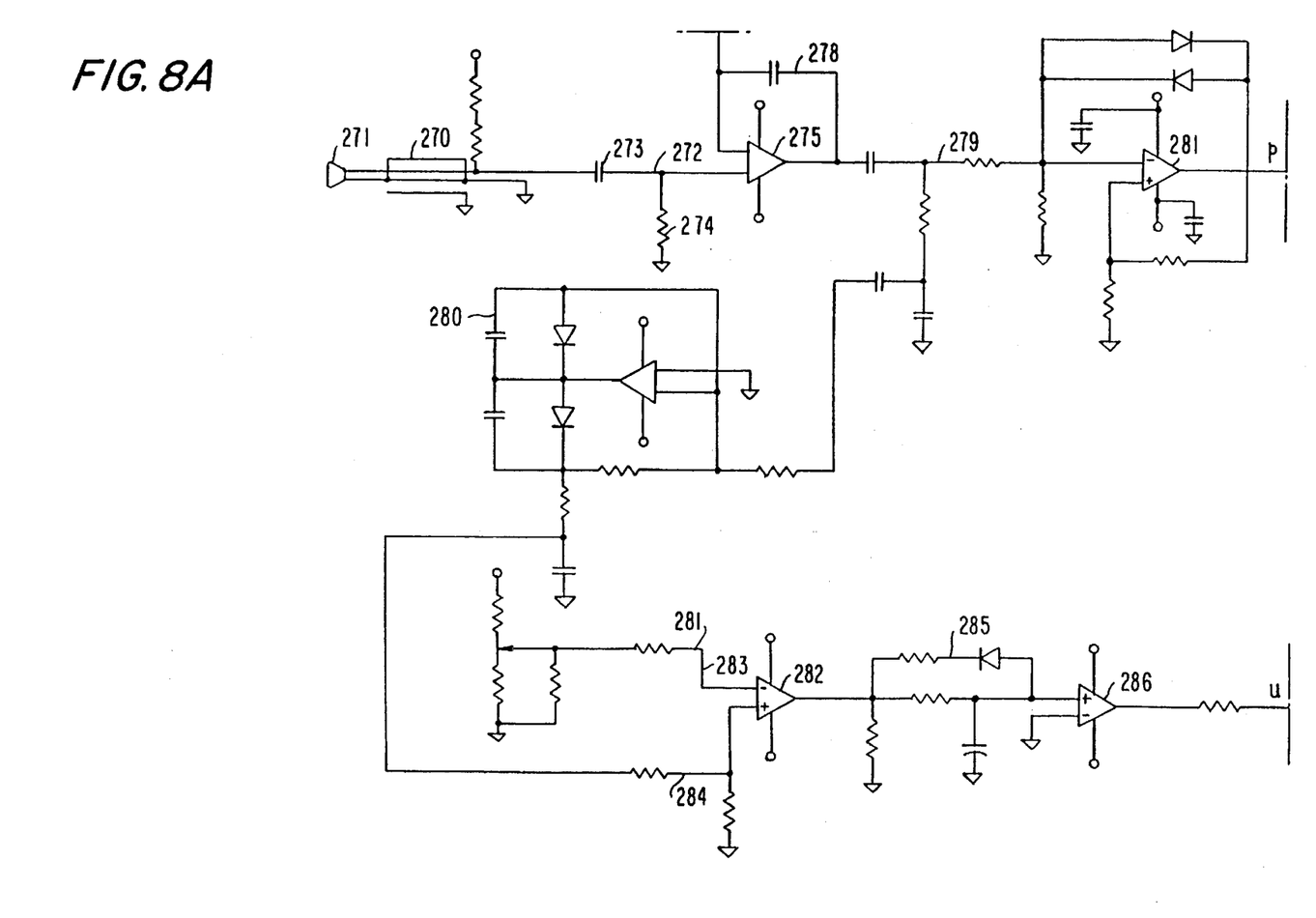
FIGS. 8a, 8b, and 8c constitute a detailed schematic diagram of the electronic components of the receiving part of the device in accordance with the second embodiment.
Figure 8B:
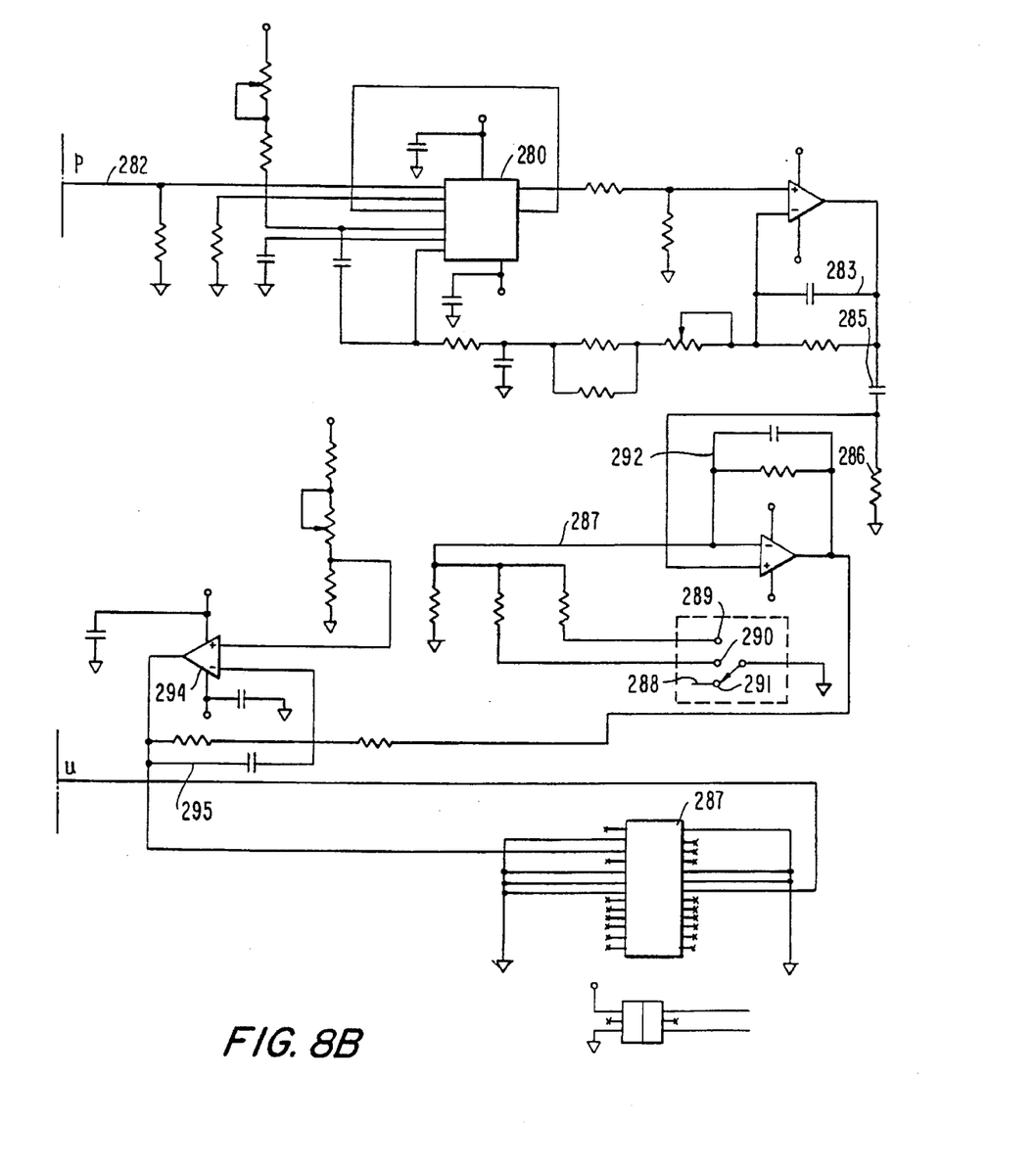
Figure 8C:
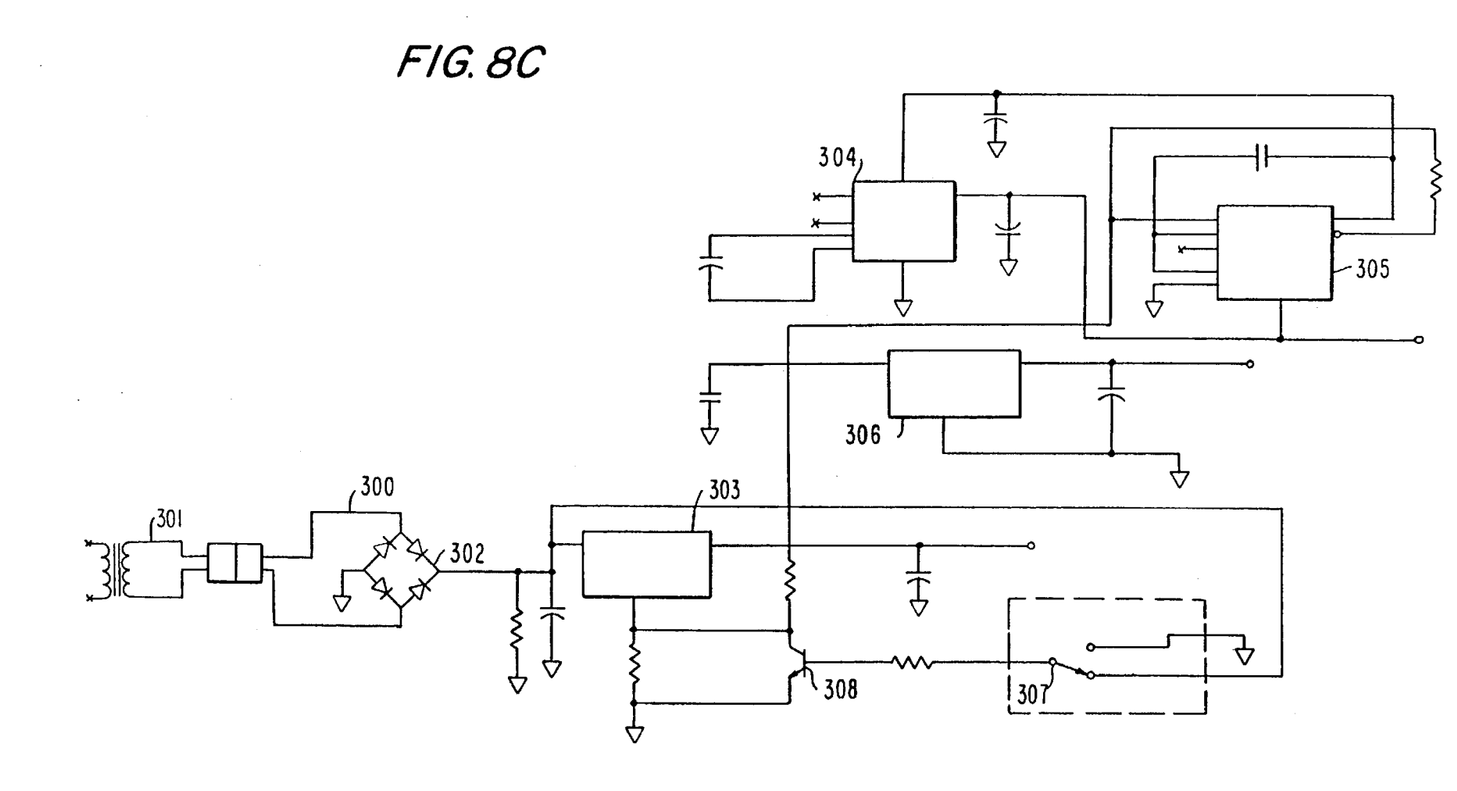

Referring to FIG. 8, a corresponding electrical schematic diagram relating to the receiving unit is illustrated. The unit includes a front end 270 having a microphone 271 which feeds a band pass filter 272 with poles at 234 Hz and 1881 Hz. The signal is then amplified through an LF347 Bifet operational amplifier 281 with an adjustable gain around 14. The filter 272 includes a capacitor 273 and resistor 274. The operational amplifier 275 feeds high pass and low pass filters 278 and 279. The high pass filter outputs to a low pass rectifier 280 forming part of a carrier detect circuit 281. The output of the rectifier feeds a comparator 282. When a carrier wave is detected, the voltage level rises. When it reaches 0.25 volt, the strip chart recorder is activated. The comparator 282 has reference inputs 283 and 284. The output is further filtered at 285 and fed to further amplification at 286 before entering sensitivity detector 287.

The phase locked loop 288 is fed by a zero crossing detector including a comparator 289 through a high frequency pass 290. The output from circuit 288 is to a low pass filter 291 and a high pass error detector 292.

Reference character 293 denotes an adjustable gain stage, including a panel switch 294 having first, second and third positions 295, 296 and 297. The output feeds another gain stage 298.

The power supply 300 (FIG. 8C) is adapted to power the above described circuitry and the strip chart recorder. It includes a transformer 301 powered by a wall outlet to provide both 15 volt and 5 volt current. The output is through a bridge rectifier 302 which feeds a regulator 303 providing the 15 volt current. It also feeds a voltage convertor 304 which supplies current to voltage regulators 305 and 306 for the 5 volt supply. A power switch 307 is manually operated in conjunction with a shut down circuit 308 which grounds the power supply if voltage output is inadequate.

Operation of the device by the patient is as described above. At the time the patient dials the telephone at the remote location, the indicator light 54 should be green. If the light is not illuminated, the patient is thereby advised that the batteries of his unit need to be replaced. When the cuff is inflated, the indicator light changes to red, and after stabilization of the system, normally requiring 5 seconds, the light will change from red to green. At this point, the system is now sending information to the remote location.

If during transmission pressure in the cuff drops to less than the standard 60 mm Hg, the indicator light will change from green to yellow, and transmission will stop. After reinflating, the indicator light will change to red. Should the pressure in the cuff be greater than 70 mm Hg, the indicator light will change to red, and the unit will automatically operate solenoid 256 to deflate the cuff until proper pressure is reached, and transmission will resume. After sufficient transmission, normally requiring a minute or two, the patient hangs up by transferring the hand set from the microphone to the dial base. When the hand set is removed thereafter, the cuff will automatically be deflated through the solenoid 256, and can then be removed, thus completing the test.

At the receiving station, upon receipt of an initial phone call, the power switch is turned to on, and the gain switch 288 is set at 1.0. When the strip chart recorder commences operation, depending upon the amplitude of the observed sine wave, the gain switch may be altered to a setting of either 2.5 or 5.0 if a very low amplitude is recorded at gain 1. After 4 full cardiac cycles are recorded, the power switch is turned to off, the trace removed from the recorder and attached to the patients records.

It may thus be seen that we have invented a novel and highly useful system by means of which many periodic visits to a physician to check arterial pressure in an area of interest are avoided. The device uses a combination of known electrical circuitry, which, in solid state form operates at very low voltages, and which may be battery powered. Since information is transmitted on a discontinuous basis, a relatively large number of patients may be monitored in selective fashion using a single subscriber line. In cases where relatively few number of patients are being monitored, it may be possible to operate the device without the use of a dedicated subscriber line at the receiving location. In addition, there is provided a simple pressure control circuitry utilizing a known LED displayed driver in combination with logic circuitry and a multiplex circuit to provide solenoid actuation.

We wish it to be understood that we do not consider the invention to be limited to the precise details of structure shown and set forth in this specification, for obvious modifications will occur to those skilled in the art to which the invention pertains.

We claim:

1. A device for transmitting data from a first location to provide a reproducible arterial wave form by telephone line transmission comprising: an inflatable cuff element adapted to engage a part of the body of a user, said cuff element including means for inflating said cuff after body engagement to a predetermined pressure value; means for indicating to the user the attainment and maintenance of said pressure value; a piezo-electric member secured to said cuff on an inner surface thereof for generating an electrical analog signal, the voltage of which varies in accordance with pulsatile change of the user; means communicating said signal to a telephone modem for transmission over a telephone line to a subscriber circuit at a second location, said second location also including a modem for converting a received signal to analog form; charting means for graphically displaying said received signal; said means indicating the obtainment and maintenance of pressure value including a solenoid relief valve, and control circuitry for actuating said valve at a point above normal operating pressure, for disabling said valve at normal operating pressure, and for reactivating said valve at an intermediate value therebetween to prevent pressure fluctuation from causing erratic performance; said means also including means for interrupting transmission of information should the pressure fall below said predetermined pressure value.

2. A device in accordance with claim 1, in which said control circuitry for actuating said solenoid relief valve is operated as plural threshold levels; a first level being at 75 mmHg for initial actuation; a second level being at 65 mmHg, where the solenoid is disabled, and wherein the device commences transmitting data; a third level being at 70 mmHg wherein the solenoid is again actuated, and a fourth level being at 60 mmHg wherein an indication is made to reinflate said cuff.

* * * * *